United States Patent
Komatsu

(10) Patent No.: US 11,106,198 B2
(45) Date of Patent: Aug. 31, 2021

(54) QUALITY CONTROL APPARATUS

(71) Applicant: FUJIFILM BUSINESS INNOVATION CORP., Tokyo (JP)

(72) Inventor: Yutaka Komatsu, Kanagawa (JP)

(73) Assignee: FUJIFILM Business Innovation Corp., Tokyo (JP)

( * ) Notice: Subject to any disclaimer, the term of this patent is extended or adjusted under 35 U.S.C. 154(b) by 184 days.

(21) Appl. No.: 16/126,543

(22) Filed: Sep. 10, 2018

(65) Prior Publication Data
US 2019/0086905 A1    Mar. 21, 2019

(30) Foreign Application Priority Data

Sep. 21, 2017  (JP) .............................. JP2017-181253

(51) Int. Cl.
*G05B 19/418* (2006.01)
*G01N 33/00* (2006.01)

(52) U.S. Cl.
CPC ....... *G05B 19/41875* (2013.01); *G01N 33/00* (2013.01); *G01N 2033/0088* (2013.01); *G05B 2219/32177* (2013.01); *G05B 2219/32368* (2013.01)

(58) Field of Classification Search
CPC .... G05B 19/41875; G05B 2219/32368; G05B 2219/32177; G01N 33/00; G01N 2033/0088
See application file for complete search history.

(56) References Cited

U.S. PATENT DOCUMENTS

| 9,058,695 B2* | 6/2015 | Cardno ................. G06T 11/206 |
| 2006/0047454 A1* | 3/2006 | Tamaki ................. G06Q 10/06 |
| | | 702/84 |

FOREIGN PATENT DOCUMENTS

| JP | 2002-251212 A | 9/2002 |
| JP | 2008-146344 A | 6/2008 |
| JP | 2015-142084 A | 8/2015 |
| WO | 2015/115426 A1 | 8/2015 |

OTHER PUBLICATIONS

May 11, 2021 Office Action issued in Japanese Patent Application No. 2017-181253.

* cited by examiner

*Primary Examiner* — Tarun Sinha
*Assistant Examiner* — Yossef Korang-Beheshti
(74) *Attorney, Agent, or Firm* — Oliff PLC

(57) ABSTRACT

A quality control apparatus includes: a test value acquisition unit that acquires test values of respective components that constitute a product; an assembling management information acquisition unit that acquires assembling management information that is information concerning assembling of the product and the components; a step-related information acquisition unit that acquires step-related information that is information related to a production step; and a display that displays a configuration diagram of the product that is hierarchically constituted by the components and shows a combination of elements that are assumed to be likely to have caused a quality defect of the product on the configuration diagram on a basis of the test values, the assembling management information, and the step-related information.

14 Claims, 13 Drawing Sheets

FIG. 2

MULTIFUNCTION PRINTER (MODEL NAME: MFP)
+TRANSFER UNIT (MODEL NAME: TRS)
  +DRUM (MODEL NAME: DR)
    +WIRE (MODEL NAME: DRWR)
    +BELT (MODEL NAME: DRBL)
  +SHIELD (MODEL NAME: SR)
  +ROLLER (MODEL NAME: RR)
+DEVELOPING UNIT (MODEL NAME: GZ)
+FIXING UNIT (MODEL NAME: TE)
+CONTROLLER (MODEL NAME: CON)

FIG. 3

| ASSEMBLING TARGET (INDIVIDUAL) | ASSEMBLING TARGET (MODEL NAME) | JOINED COMPONENT (INDIVIDUAL) | JOINED COMPONENT (MODEL NAME) | DATE AND TIME OF ASSEMBLING | ASSEMBLING PLACE |
|---|---|---|---|---|---|
| MFP201703010001 | MFP | TRS201703010001 | TRS | MARCH 1, 2017 10:10 | TRANSFER UNIT ASSEMBLING CELL |
| MFP201703010001 | MFP | GZ201703010001 | GZ | MARCH 1, 2017 10:30 | DEVELOPING UNIT ASSEMBLING CELL |
| MFP201703010001 | MFP | TE201703010001 | TE | MARCH 1, 2017 10:50 | FIXING UNIT ASSEMBLING CELL |
| MFP201703010001 | MFP | CON201703010001 | CON | MARCH 1, 2017 11:10 | CONTROLLER ASSEMBLING CELL |
| TRS201703010001 | TRS | DR2017aaaxxx | DR | MARCH 1, 2017 9:10 | DRUM ASSEMBLING CELL |
| TRS201703010001 | TRS | SR2017aaaxxx | SR | MARCH 1, 2017 9:20 | SHIELD ASSEMBLING CELL |
| TRS201703010001 | TRS | RR2017aaaxxx | RR | MARCH 1, 2017 9:30 | ROLLER ASSEMBLING CELL |
| DR2017aaaxxx | DR | DRWR1234 | DRWR | MARCH 1, 2017 9:05 | WIRE WORKPLACE |
| DR2017aaaxxx | DR | DRBL3344 | DR | MARCH 1, 2017 9:06 | BELT ASSEMBLING CELL |
| MFP201703010002 | MFP | TRS201703010002 | TRS | MARCH 2, 2017 10:10 | TRANSFER UNIT ASSEMBLING CELL |
| MFP201703010002 | MFP | GZ201703010002 | GZ | MARCH 2, 2017 10:30 | DEVELOPING UNIT ASSEMBLING CELL |
| MFP201703010002 | MFP | TE201703010002 | TE | MARCH 2, 2017 10:50 | FIXING UNIT ASSEMBLING CELL |
| MFP201703010002 | MFP | CON201703010002 | CON | MARCH 2, 2017 11:10 | CONTROLLER ASSEMBLING CELL |
| TRS201703010002 | TRS | DR2017bbbyyy | DR | MARCH 2, 2017 9:10 | DRUM ASSEMBLING CELL |
| TRS201703010002 | TRS | SR2017bbbyyy | SR | MARCH 2, 2017 9:20 | SHIELD ASSEMBLING CELL |
| TRS201703010002 | TRS | RR2017bbbyyy | RR | MARCH 2, 2017 9:30 | ROLLER ASSEMBLING CELL |
| DR2017bbbyyy | DR | DRWR2222 | DRWR | MARCH 2, 2017 9:05 | WIRE WORKPLACE |
| DR2017bbbyyy | DR | DRBL2222 | DR | MARCH 2, 2017 9:06 | BELT ASSEMBLING CELL |
| ... | | | | | |

FIG. 4

| IDENTIFICATION INFORMATION | TEST VALUE NAME | TEST VALUE |
| --- | --- | --- |
| MFP201703010001 | NUMBER OF SHEETS OUTPUT PER MINUTE | 20 |
| MFP201703010002 | NUMBER OF SHEETS OUTPUT PER MINUTE | 7 |
| MFP201703010003 | NUMBER OF SHEETS OUTPUT PER MINUTE | 21 |
| TRS201703010001 | TEST VALUE X | 100 |
| TRS201703010002 | TEST VALUE X | 200 |
| TRS201703010001 | TEST VALUE Y | 10 |
| TRS201703010002 | TEST VALUE Y | 10 |
| GZ201703010001 | TEST VALUE G | 0.1 |
| GZ201703010002 | TEST VALUE G | 0.11 |
| TE201703010001 | TEST VALUE T | 50 |
| TE201703010002 | TEST VALUE T | 50 |
| DR2017aaaxxx | ROTATION SPEED | 180 |
| DR2017bbbyyy | ROTATION SPEED | 100 |
| SR2017aaaxxx | MEASUREMENT VALUE S | 60 |
| SR2017bbbyyy | MEASUREMENT VALUE S | 60 |
| RR2017aaaxxx | ROLLER LUBRICATION DEGREE | 10 |
| RR2017bbbyyy | ROLLER LUBRICATION DEGREE | 12 |
| DRWR1234 | WIRE ELONGATION | 0.1 |
| DRWR2222 | WIRE ELONGATION | 0.1 |
| DRBL3344 | BELT ELONGATION | 0.2 |
| DRBL2222 | BELT ELONGATION | 0.19 |

FIG. 5

| INFORMATION IDENTIFICATION INFORMATION | KIND OF STEP | DATE AND TIME OF START OF USE | DATE AND TIME OF END OF USE | ATTRIBUTE NAME | ATTRIBUTE VALUE |
|---|---|---|---|---|---|
| MEASURING DEVICE X | DRUM ASSEMBLING CELL | MARCH 1, 2017 0:00 | MARCH 31, 2017 0:00 | DATE OF FINAL ADJUSTMENT | JANUARY 1, 2017 |
| ASSEMBLING APPARATUS C1 | DRUM ASSEMBLING CELL | MARCH 1, 2017 0:00 | MARCH 2, 2017 0:00 | ARM LUBRICATION DEGREE | 98% |
| ASSEMBLING APPARATUS C2 | DRUM ASSEMBLING CELL | MARCH 2, 2017 0:00 | MARCH 3, 2017 0:00 | ARM LUBRICATION DEGREE | 99% |
| WORKER A | DRUM ASSEMBLING CELL | MARCH 1, 2017 0:00 | MARCH 2, 2017 0:00 | LEARNING LEVEL | 200 |
| WORKER B | DRUM ASSEMBLING CELL | MARCH 2, 2017 0:00 | MARCH 3, 2017 0:00 | LEARNING LEVEL | 10 |

FIG. 8

| TEST VALUE NAME | TEST VALUE | AVERAGE | DEVIATION RATE | RESULT OF DETERMINING PROCESS CONCERNING PECULIAR VALUE |
|---|---|---|---|---|
| TEST VALUE X | 200 | 150 | 0.333333333 | ✓ |
| TEST VALUE Y | 10 | 10 | 0 | |
| TEST VALUE G | 0.11 | 0.105 | 0.047619048 | |
| TEST VALUE T | 50 | 50 | 0% | |
| ROTATION SPEED | 100 | 140 | −29% | ✓ |
| MEASUREMENT VALUE S | 60 | 60 | 0% | |
| ROLLER LUBRICATION DEGREE | 12 | 11 | 9% | |
| WIRE ELONGATION | 0.1 | 0.1 | 0% | |
| BELT ELONGATION | 0.19 | 0.195 | −3% | |

FIG. 9

| ATTRIBUTE NAME | ATTRIBUTE VALUE | AVERAGE | DEVIATION RATE | RESULT OF DETERMINING PROCESS CONCERNING PECULIAR VALUE |
|---|---|---|---|---|
| DATE OF FINAL ADJUSTMENT | 42736 | 42736 | 1900/1/0 | |
| ARM LUBRICATION DEGREE | 0.99 | 0.985 | 0.005076142 | |
| LEARNING LEVEL | 10 | 105 | −0.904761905 | ✓ |

QUALITY CONTROL APPARATUS

CROSS-REFERENCE TO RELATED APPLICATIONS

This application is based on and claims priority under 35 USC 119 from Japanese Patent Application No. 2017-181253 filed Sep. 21, 2017.

BACKGROUND

(i) Technical Field

The present invention relates to a quality control apparatus.

(ii) Related Art

In a case where a product constituted by plural components has a quality defect, it is requested that an element that is a cause of the quality defect be specified. The element that is a cause of the quality defect is, for example, a component that constitutes the product or a step of assembling components.

SUMMARY

According to an aspect of the invention, there is provided a quality control apparatus including: a test value acquisition unit that acquires test values of respective components that constitute a product; an assembling management information acquisition unit that acquires assembling management information that is information concerning assembling of the product and the components; a step-related information acquisition unit that acquires step-related information that is information related to a production step; and a display that displays a configuration diagram of the product that is hierarchically constituted by the components and shows a combination of elements that are assumed to be likely to have caused a quality defect of the product on the configuration diagram on a basis of the test values, the assembling management information, and the step-related information.

BRIEF DESCRIPTION OF THE DRAWINGS

An exemplary embodiment of the present invention will be described in detail based on the following figures, wherein:

FIG. 2 illustrates an example of a configuration of a product constituted by plural components;

FIG. 3 illustrates a data example of an assembling management information DB;

FIG. 4 illustrates a data example of a test value DB;

FIG. 5 illustrates a data example of a step-related information DB;

FIG. 8 illustrates an example of test values that are peculiar values;

FIG. 9 illustrates an example of peculiar values in assembling work;

DETAILED DESCRIPTION

An exemplary embodiment of the present invention is described in detail below with reference to the attached drawings.

Functional Configuration of Quality Control Apparatus

Figure 1:
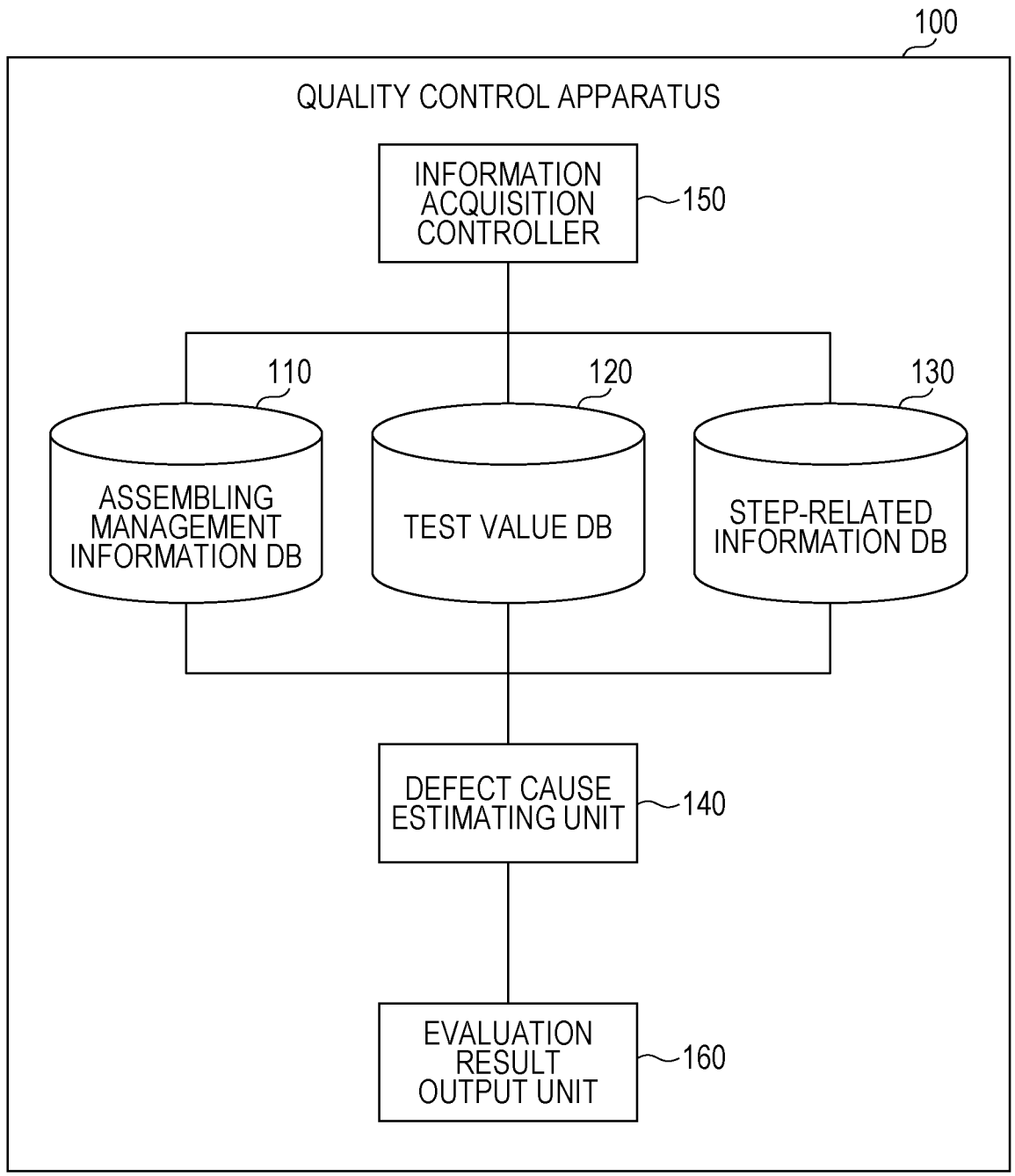
FIG. 1 illustrates a functional configuration of a quality control apparatus according to the present exemplary embodiment.

FIG. 1 illustrates a functional configuration of a quality control apparatus according to the present exemplary embodiment. A quality control apparatus 100 according to the present exemplary embodiment includes an assembling management information database (DB) 110, a test value database (DB) 120, a step-related information database (DB) 130, a defect cause estimating unit 140, an information acquisition controller 150, and an evaluation result output unit 160. The quality control apparatus 100 is connected to a control device and a management device (not illustrated) for a product production line or the like and exchanges data with these devices.

The assembling management information DB 110 is a database in which information (assembling management information) concerning assembling of a product and components is managed. In the assembling management information DB 110, identification information of each component that constitutes a product, information specifying a step of joining the component, and contents of the step are stored as assembling management information in association with one another. The identification information of each component is information for identifying the individual component. The identification information of each component may be, for example, a serial number allocated to the individual component. The information specifying a step of joining a component is information indicative of a date and a time and a place of the joining step. The information indicative of a place of the joining step is, for example, information specifying a production cell or a production line. In a case where a cell or a line is used as the information on the place, the kind of step is indicated by the information on the place. The contents of the step are information indicating which component is joined to which component.

FIG. 2 illustrates an example of a configuration of a product constituted by plural components. In FIG. 2, the configuration of the product is illustrated as a tree structure based on assembling of the components. In this way, the product can be grasped as being constituted by hierarchically-assembled components. That is, a hierarchical structure of the product is grasped in a component assembling relationship such that a component in a second level is joined to a component in a first level, and a component in a third level is joined to the component in the second level. For this purpose, the structure of the product is expressed by a tree diagram like the one illustrated in FIG. 2.

FIG. 2 illustrates an example of a configuration of a multifunction printer. In the tree diagram illustrated in FIG. 2, a node represents the product or a component. An edge between nodes represents an assembling relationship between the product and a component or between components. In the example illustrated in FIG. 2, a component indicated by a right node is joined to the product or a component indicated by a left node connected to the right node through an edge. FIG. 2 shows that a transfer unit (model name: TRS), a developing unit (model name: GZ), a fixing unit (model name: TE), and a controller (model name: CON) are joined to a multifunction printer (model name: MFP) that is a final product. A drum (model name: DR), a shield (model name: SR), and a roller (model name: RR) are joined to the transfer unit (model name: TRS). A wire (model name: DRWR) and a belt (model name: DRBL) are joined to the drum (model name: DR).

FIG. 3 illustrates a data example of the assembling management information DB 110. FIG. 3 illustrates an example of assembling management information of the product (multifunction printer) illustrated in FIG. 2. In the example illustrated in FIG. 3, individual information and model name information of an "assembling target" to which a component is joined in an assembling step, individual information and model name information of a "joined component" that is joined to the assembling target, "assembling date and time" that is date and time of the assembling step, and an "assembling place" that is a place of the assembling step are recorded. For example, in the first row, "MFP201703010001" that is identification information indicative of the multifunction printer is recorded in "assembling target (individual)", and "MFP" that is a model name of the multifunction printer is recorded in "assembling target (model name)". Furthermore, "TRS201703010001" that is identification information indicative of a joined component is recorded in "joined component (individual)", and "TRS" that is a model name indicative of the transfer unit is recorded in "joined component (model name)". Furthermore, "Mar. 1, 2017 10:10" is recorded in "assembling date and time", and "transfer unit assembling cell" is recorded in "assembling place". That is, the information managed in this row shows that a step of joining the transfer unit "TRS201703010001" to the multifunction printer "MFP201703010001" was performed at 10:10 on Mar. 1, 2017. Since information on the "assembling target" and information on the "joined component" are recorded as described above, contents of the step is also recorded.

The test value DB 120 is a database in which test values of the product and the components thereof are managed. In the test value DB 120, identification information of the product and the components, names of test values (test value names) obtained by various tests conducted on the product and the components, and test values obtained by the tests are recorded in association with one another. The test value names are set in accordance with kinds (test items) of conducted tests. Accordingly, in a case where a new test item for a certain component is added, a test value name and a test value concerning the component are added.

FIG. 4 illustrates a data example of the test value DB 120. FIG. 4 illustrates an example of test values for the product (multifunction printer) and the components thereof illustrated in FIG. 2. FIG. 4 illustrates some of test values for the product and the components. For example, in the first row, "MFP201703010001" that is identification information indicative of the multifunction printer is recorded in "identification information". Furthermore, "number of sheets output per minute" indicating that a test item is the number of sheets output per minute is recorded in "test value name", and "20" indicative of the number of sheets output per minute (test value) is recorded in "test value". In the second and third rows, the number of sheets output per minute is recorded for a multifunction printer given identification information "MFP201703010002" and a multifunction printer given identification information "MFP201703010003". The fourth through seventh rows show that two kinds of test items "test value X" and "test value Y" are tested for each of a transfer unit given identification information "TRS201703010001" and a transfer unit given identification information "TRS201703010002". Furthermore, the fourth through seventh rows show that a test value of the "test value X" is "100" and a test value of the "test value Y" is "10" as for the identification information "TRS201703010001" and show that a test value of the "test value X" is "200" and a test value of the "test value Y" is "10" as for the identification information "TRS201703010002".

The step-related information DB 130 is a database in which information (step-related information) related to a production step is managed. The step-related information is information on an apparatus used for each step and a worker engaged in each step. In the step-related information DB 130, a combination of information identification information, a kind of step, a working period in the step, and attribute information is stored as the step-related information. The information identification information is identification information for identifying the combination of pieces of information. Contents of the information is not limited in particular since the combination of pieces of information need just be identified. For example, identification information of an apparatus used in a corresponding step or a worker engaged in the corresponding step may be used as the information identification information. The kind of step is information indicative of a kind of conducted step. The information on a kind of step may be, for example, information indicative of a cell or a line in which the step is conducted. The working period in the step is an operating period of an apparatus used in the step or a working period of a worker engaged in the step. In a case where identification information of an apparatus or a worker is used as the information identification information, a working period of work using an apparatus or conducted by a worker specified by the identification information is recorded. The attribute information is information indicative of an attribute of an apparatus used in the step or a worker engaged in the step. As the attribute information, various kinds of information concerning work may be recorded in accordance with a corresponding apparatus or worker. For example, information on date and time of installation or maintenance or an operating state of an apparatus having a movable part may be recorded as an attribute of the apparatus. As an attribute of a worker, a learning level measured by a skill test or the like, a period of experience of work or the number of times of work in the step, or the like may be recorded.

FIG. 5 illustrates a data example of the step-related information DB 130. FIG. 5 illustrates an example of step-related information related to a production step of the product (multifunction printer) illustrated in FIG. 2. In the example illustrated in FIG. 5, "information identification information", "kind of step", "date and time of start of use", "date and time of end of use", "attribute name", and "attribute value" are recorded. In the "information identification information", identification information (a name in the example illustrated in FIG. 5) of an apparatus used for work or a worker engaged in the work is recorded. In the "kind of step", identification information (a name in the example illustrated in FIG. 5) of a cell in which a corresponding step was performed is recorded. The "date and time of start of use" and "date and time of end of use" indicate a working period in the step. The "attribute name" and "attribute value" indicate attribute information of an apparatus or a worker indicated by the "information identification information".

For example, in the first row, "measuring apparatus X" is recorded in the "information identification information", and "drum assembling cell" is recorded in the "kind of step". Furthermore, "Mar. 1, 2017 0:00" is recorded in the "date and time of start of use", and "Mar. 31, 2017 0:00" is recorded in the "date and time of end of use". Furthermore, "date of final adjustment" is recorded in the "attribute name", and "Jan. 1, 2017" is recorded in the "attribute value". That is, the first row shows that the measuring apparatus X operated from midnight on Mar. 1, 2017 to midnight on Mar. 31, 2017 in a step performed in a drum assembling cell and that last adjustment of the measuring apparatus X was performed in January 2017. In the second and third rows, a degree of lubrication of an arm is recorded as attribute information concerning assembling apparatuses C1 and C2 used in the step performed in the drum assembling cell. Similarly, in the fourth and fifth rows, a learning level is recorded as attribute information concerning workers A and B in the step performed in the drum assembling cell. Comparison between the second row and the fourth row shows that the worker A is a worker during operation of the assembling apparatus C1, and comparison between the third row and the fifth row shows that the worker B is a worker during operation of the assembling apparatus C2.

The defect cause estimating unit 140 is a processing unit that estimates a cause of a quality defect of a product on the basis of the assembling management information, test values, and step-related information. The defect cause estimating unit 140 estimates a cause of a defect by specifying a combination of elements such as a component and a step (work) that meet a predetermined condition on the basis of a degree of deviation of a value such as a test value or an attribute value (attribute information) of the step-related information from a standard value. That is, the defect cause estimating unit 140 is an example of a specifying unit. The combination of elements is determined on the basis of an assembling relationship among the components that constitute the product. The standard value is a standard value which a test value or an attribute value can take. Examples of the standard value include an average, a median, a mode, or the like of test values or attribute values in normal products. What kind of value is employed as the standard value is specifically determined in accordance with the kind of element, kind of test value or attribute value, setting in quality control, and the like. The degree of deviation is a degree to which an obtained test value or attribute value is deviated from a standard value of the test value or attribute value. The degree of deviation is, for example, a rate of deviation from an average. What kind of value is employed as the degree of deviation is specifically determined in accordance with the kind of element, kind of test value or attribute value, setting in quality control, and the like.

In general, in a case where test values or attribute values of elements such as individual components or steps (work) concerning a product having a quality defect are within a normal range, these elements are not regarded as a cause of the quality defect. However, in a case where test values or attribute values of individual components or steps (work) are deviated from standard values to a degree that is not regarded as being abnormal, such plural elements can combine to cause the quality defect.

In view of this, in the present exemplary embodiment, a peculiar value is set as a standard of evaluation of a test value or an attribute value, and the defect cause estimating unit 140 detects an element (hereinafter referred to as a peculiar value element) whose test value or attribute value is a peculiar value. In a case where a combination of plural peculiar value elements meets a specific condition, the defect cause estimating unit 140 specifies the combination of plural peculiar value elements as a candidate for a cause of a defect (hereinafter referred to as a defect cause candidate). That is, the peculiar value elements that constitute the defect cause candidate are elements that are assumed to be likely to have caused the quality defect. The peculiar value is a test value or an attribute value of an element such as a component or a step (work) that is within a normal range (is not abnormal) but whose degree of deviation from a standard value meets a specific condition. The condition for the peculiar value is specifically determined in accordance with the kind of element, kind of test value or attribute value, setting in quality control, and the like. For example, the condition can be sometimes set relatively on the basis of a test value or an attribute value concerning an element of the same kind. Alternatively, a fixed value can be sometimes set for each component or step (work).

In a case where plural combinations of peculiar value elements are present as defect cause candidates, the defect cause estimating unit 140 determines priorities of the combinations of peculiar value elements in an order starting from a combination that is regarded as being most likely to be a defect cause in accordance with a specific rule. Details of detection of a peculiar value element, estimation of a defect cause, and determination of priorities by the defect cause estimating unit 140 will be described later.

The information acquisition controller 150 is a processing unit that acquires assembling management information, test values, and step-related information and causes the assembling management information, the test values, and the step-related information to be stored in the assembling management information DB 110, the test value DB 120, and the step-related information DB 130. That is, the information acquisition controller 150 is an example of an assembling management information acquisition unit, an example of a test value acquisition unit, and an example of step-related information acquisition unit. The information acquisition controller 150 acquires the assembling management information, for example, from an assembling work management system. Furthermore, the information acquisition controller 150 acquires the test values, for example, from a system for management of various sensors provided on a site such as a cell or a line or directly from the sensors. Furthermore, the information acquisition controller 150 acquires the step-related information, for example, from a step or work management system.

The evaluation result output unit 160 is a unit that outputs information on a defect cause candidate (a combination of peculiar value elements) estimated by the defect cause estimating unit 140. The evaluation result output unit 160 outputs information on a defect cause candidate as a group of elements that are assumed to be likely to have caused a quality defect of a product. For example, the evaluation result output unit 160 presents information on a defect cause candidate by displaying, on a display device, a diagram or a table representing an assembling structure of components in the product so that a part regarded as the defect cause candidate is displayed in a form different from the other part. That is, the evaluation result output unit 160 is an example of an output unit and is an example of a display. The diagram displayed on the display device may be, for example, a tree diagram like the one illustrated in FIG. 2.

Hardware Configuration of Computer

Figure 6:
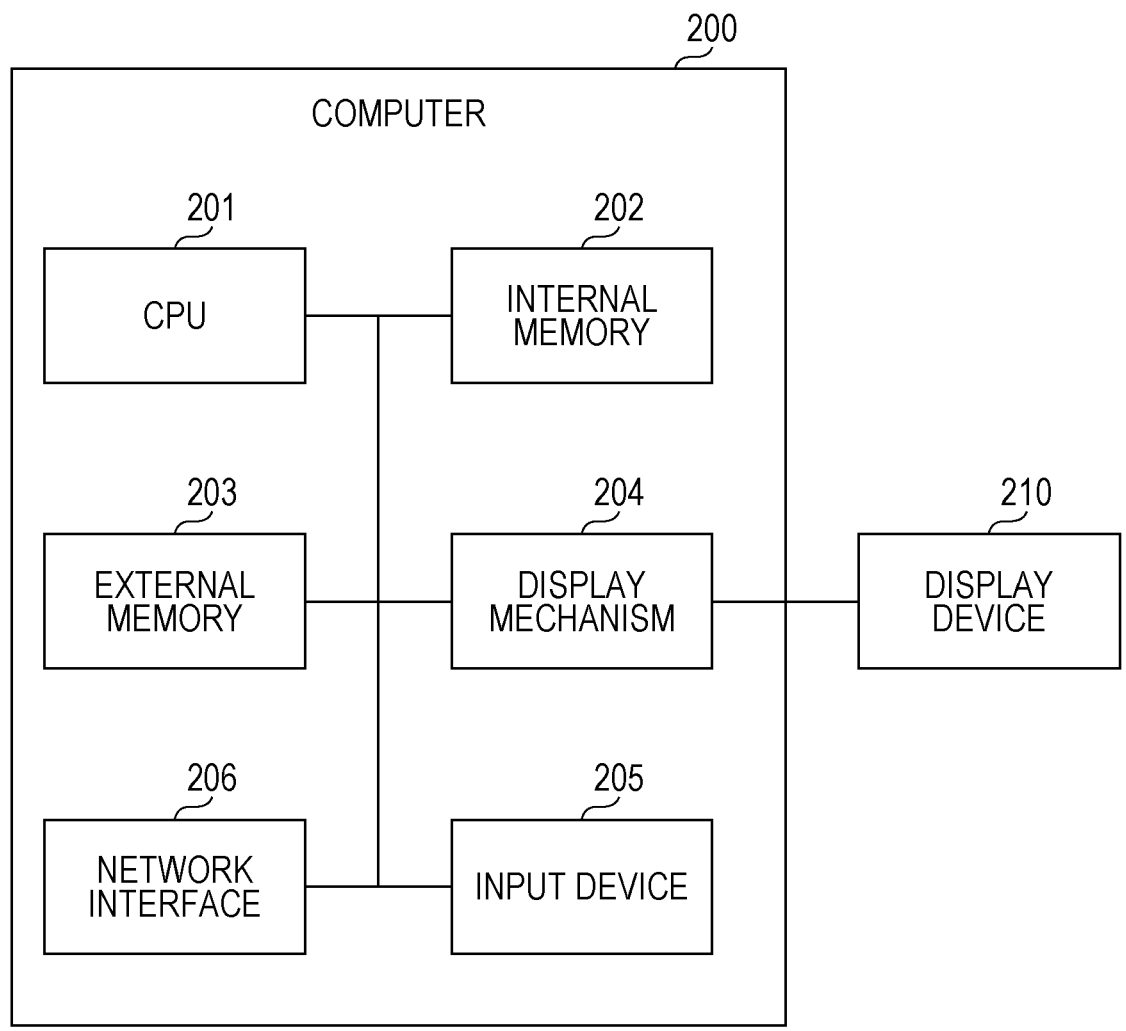
FIG. 6 illustrates an example of a hardware configuration of a computer used as the quality control apparatus.

FIG. 6 illustrates an example of a hardware configuration of a computer used as the quality control apparatus 100. A computer 200 illustrated in FIG. 6 includes a central processing unit (CPU) 201 that is a computing unit, and an internal memory 202 and an external memory 203 that are memories. The CPU 201 executes a program stored in the external memory 203 by loading the program into the internal memory 202. The internal memory 202 is, for example, a random access memory (RAM). The external memory 203 is, for example, a magnetic disc device or a solid state drive (SSD). Furthermore, the computer 200 includes a display mechanism 204 for display output on a display device (display) 210 and an input device 205 that is used for input operation by an operator of the computer 200. The input device 205 is, for example, a keyboard or a mouse. The computer 200 includes a network interface 206 for connection with a network. The configuration of the computer 200 illustrated in FIG. 6 is merely an example, and the computer used in the present exemplary embodiment is not limited to the example of the configuration illustrated in FIG. 6. For example, the computer 200 may include, as a memory device, a non-volatile memory such as a flash memory or a read only memory (ROM).

In the quality control apparatus 100 illustrated in FIG. 1, the assembling management information DB 110, the test value DB 120, and the step-related information DB 130 are provided, for example, by the internal memory 202 or the external memory 203. The defect cause estimating unit 140 is provided, for example, by the CPU 201 that is controlled in accordance with the program. The information acquisition controller 150 is provided, for example, by the CPU 201 that is controlled in accordance with the program and the network interface 206. The evaluation result output unit 160 is provided, for example, by the CPU 201 and the display mechanism 204 that are controlled in accordance with the program and the display device 210.

Operation of Quality Control Apparatus

Figure 7:
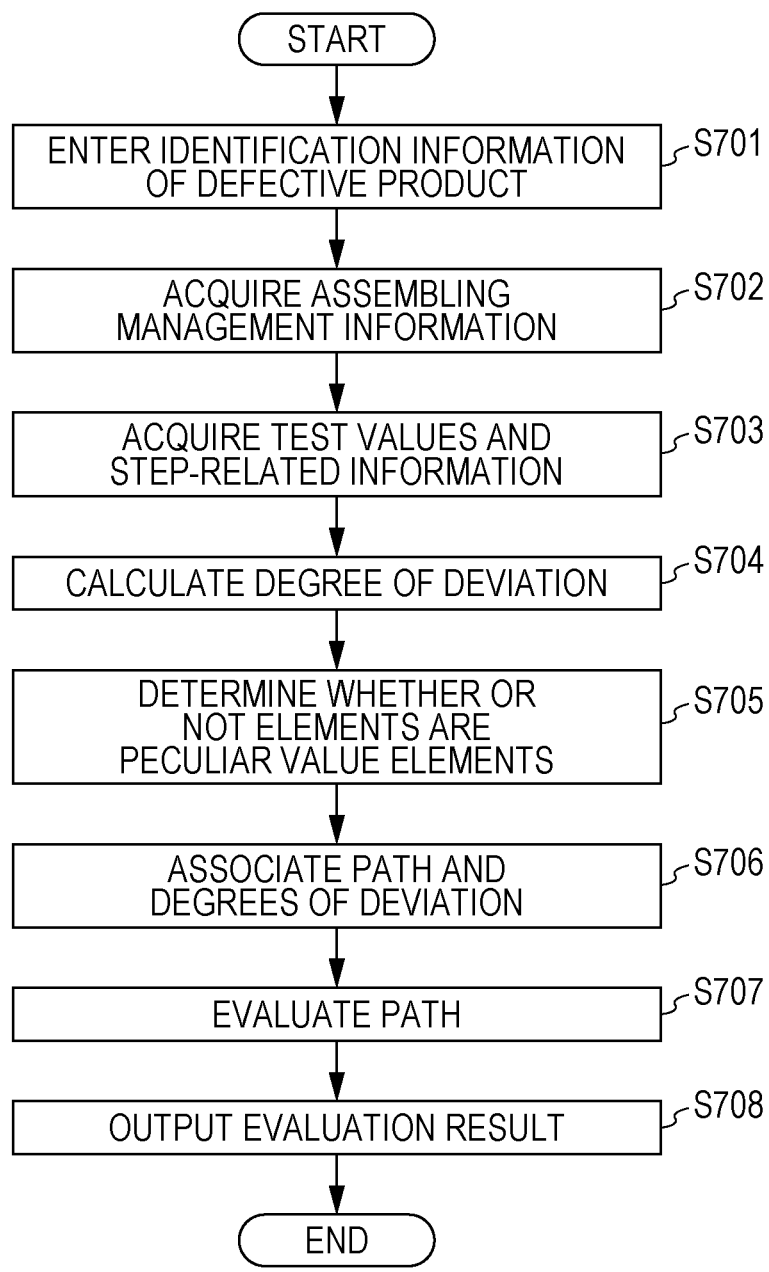
FIG. 7 is a flowchart illustrating operation of the quality control apparatus.

FIG. 7 is a flowchart illustrating operation of the quality control apparatus 100. In this example, it is assumed that the information acquisition controller 150 has acquired assembling management information, test values, and step-related information and has caused the assembling management information, test values, and step-related information to be stored in the assembling management information DB 110, the test value DB 120, and the step-related information DB 130.

In a case where an abnormality (quality defect) of a product is detected, identification information of the product (defective product) in which the abnormality has been detected is entered in the quality control apparatus 100 by a user of the quality control apparatus 100 (S701). When the identification information of the defective product is entered in the quality control apparatus 100, the defect cause estimating unit 140 acquires assembling management information of the product from the assembling management information DB 110 on the basis of the identification information of the product (S702).

Next, the defect cause estimating unit 140 specifies components that constitute the product and date and time and a place of assembling work on the basis of the assembling management information. Then, the defect cause estimating unit 140 acquires information concerning the components that constitute the product and the work from the test value DB 120 and the step-related information DB 130 on the basis of the specified information (S703). Specifically, the defect cause estimating unit 140 acquires test values of the components from the test value DB 120 and acquires attribute information of an apparatus used for the work or a worker from the step-related information DB 130.

Next, the defect cause estimating unit 140 calculates a degree of deviation from a standard value for each of the acquired pieces of information (S704). Then, the defect cause estimating unit 140 determines whether or not each element such as a component or a step (work) is a peculiar value element on the basis of a result of calculation of the degree of deviation (S705). In this step, whether or not a test value of each component is a peculiar value and whether or not attribute values of an apparatus and a worker concerning work performed on the component are peculiar values are determined.

Next, the defect cause estimating unit 140 associates the degree of deviation calculated in S704 and a result of the determining process in S705 with a path representing a relationship between the product and a component or between components in a component assembling structure of the product to be processed (S706). Specifically, when a path is specified, the defect cause estimating unit 140 associates, with the path, degrees of deviation and results of the determining process concerning test values of components connected through the path and degrees of deviation and results of the determining process concerning attribute information of an apparatus and a worker in work performed on these components. The path represents an assembling relationship between the product and a component or between components. The path is set between different levels of a hierarchical structure in the assembling relationship among the product and components. In other words, the path represents not a relationship between plural components joined to the same component (i.e., in the same level), but a relationship between a component in a certain level and a component in a subordinate level joined to the component. Furthermore, the path represents not only a direct assembling relationship, but also an assembling relationship among plural stages. Specifically, in a case where a component B is joined to a component A and a component C is joined to the component B, a path "component A-component B-component C" is formed. Accordingly, degrees of deviation and results of the determining process concerning test values of the component A, the component B, and the component C and degrees of deviation and results of the determining process concerning attribute information of an apparatus and a worker in the assembling work in which the component A is joined to the component B and in the assembling work in which the component C is joined to the component B are associated with this path.

Next, the defect cause estimating unit 140 evaluates each path of the component assembling structure of the product on the basis of information on the associated degrees of deviation and results of the determining process (S707). Specifically, the defect cause estimating unit 140 determines whether or not components and work specified by the path is a defect cause candidate and determines a priority of the defect cause candidate. Then, the evaluation result output unit 160 outputs a result of the evaluation conducted by the defect cause estimating unit 140 (S708).

Example of Determining Process concerning Peculiar Value

A determining process concerning a peculiar value is described by taking a specific example. In the present exemplary embodiment, it is determined whether or not a test value of a component that constitutes a product and attribute information of an apparatus used for work and a worker engaged in the work in a step for production of the product are peculiar values. Although it is determined whether or not a test value and an attribute value are peculiar values in this example, a component and work that are peculiar value elements may be given a score in accordance with degrees of deviation of these values from standard values. For example, a higher score is given as a degree of deviation becomes larger. A value of a degree of deviation itself may be given as a score. In this way, it is possible to determine not only whether or not a test value and an attribute value are peculiar values, but also a degree to which the test value and the attribute value are deviated from standard values on the basis of given scores.

FIG. 8 illustrates an example of test values that are peculiar values. FIG. 8 illustrates peculiar values specified on the basis of the data example of the test value DB 120 illustrated in FIG. 4. In FIG. 8, "test value name", "test value", "average", "deviation rate", and "result of determining process concerning peculiar value" are associated with one another. The "average" is an average of managed test values of all components of the same kinds joined to products of the same kinds. The "deviation rate" is a deviation rate of a test value from the average. It is assumed here that an abnormality has been detected in the multifunction printer given identification information "MFP201703010002" illustrated in FIG. 4. Furthermore, it is assumed that a test value name "test value X" in the fifth row, a test value name "test value Y" in the seventh row, a test value name "test value G" in the ninth row, a test value name "test value T" in the eleventh row, a test value name "rotation speed" in the thirteenth row, a test value name "measurement value S" in the fifteenth row, a test value name "roller lubrication degree" in the seventeenth row, a test value name "wire elongation" in the nineteenth row, and a test value name "belt elongation" in the twenty-first row in FIG. 4 are test values concerning components that constitute the multifunction printer given identification information "MFP201703010002". In FIG. 8, these test value names and test values thereof are extracted, and corresponding averages and deviation rates and results of the determining process concerning a peculiar value are illustrated.

In FIG. 8, a deviation rate of a test value of the test value name "test value X" from an average is 33%. A deviation rate of a test value of the test value name "rotation speed" from an average is −29%. Deviation rates of test values specified by the other test value names from averages are less than ±10%. This clearly shows that only the deviation rates of the test value X and rotation speed are markedly large. Therefore, the defect cause estimating unit 140 determines that the test values of the test value X and rotation speed are peculiar values. In this example, the defect cause estimating unit 140 determines that a test value that has a relatively large deviation rate is a peculiar value by comparing deviation rates of the test values. Alternatively, it is also possible to determine that a test value is a peculiar value in a case where an absolute value of a deviation rate of the test value is larger than a predetermined threshold value. In this case, the threshold value may be set for each test value name. Which determining method is used is determined in accordance with a kind of component, kind of test value name, setting in quality control, and the like.

FIG. 9 illustrates an example of a peculiar value in assembling work. FIG. 9 illustrates a peculiar value specified on the basis of the data example of the step-related information DB 130 illustrated in FIG. 5. In FIG. 9, "attribute name", "attribute value", "average", "deviation rate", and "result of determining process concerning peculiar value" are associated with one another. The "average" is an average of managed attribute values of all work of the same kind in an assembling step performed on products of the same kind. The "deviation rate" is a deviation rate of an attribute value from an average. In this example, pieces of step-related information indicated by the information identification information "measuring apparatus X", "assembling apparatus C2", and "worker B" are information concerning work performed in a production step for the product in which an abnormality has been detected. In FIG. 9, attribute names and attribute values of these pieces of step-related information are extracted, and corresponding averages and deviation rates and results of the determining process concerning a peculiar value are illustrated.

In FIG. 9, a deviation rate of an attribute value of an attribute name "learning level" from an average is −90%. Deviation rates of attribute values specified by the other attribute value names from averages are 1% or less. This clearly shows that only the deviation rate of the learning level is markedly large. Therefore, the defect cause estimating unit 140 determines that the attribute value of the learning level of the worker B is a peculiar value. In this example, it is determined that an attribute value that has a relatively large deviation rate is a peculiar value by comparing deviation rates of attribute values. Alternatively, it is also possible to determine that an attribute value is a peculiar value in a case where an absolute value of a deviation rate of the attribute value is larger than a predetermined threshold value. In this case, the threshold value may be set for each attribute name. Which determining method is used is determined in accordance with a kind of work, a kind of attribute name, setting in quality control, and the like.

Example of Evaluation of Path

Next, evaluation of a path is described by taking a specific example. In the present exemplary embodiment, a path including plural nodes (components) is evaluated, and a path constituted by successive nodes that are peculiar value elements is regarded as a defect cause candidate. In a case where there are plural paths that are defect cause candidates, the defect cause candidates are given priorities on the basis of a predetermined standard. A rule for determining the defect cause priorities is determined in accordance with a kind of product or component, setting in quality control, and the like. For example, a longer path (a path constituted by a larger number of successive nodes that are peculiar value elements) is given a higher priority. In a case where there are paths having the same length, a path closer to a product (a root node) is given a higher priority. In a case where there are paths having the same length and located at the same position (level), a priority of each of the paths is determined on the basis of degrees of deviation of peculiar values of nodes included in the path. Specifically, for example, an average of degrees of deviation of peculiar values of respective nodes in one path and an average of degrees of deviation of peculiar values of respective nodes in another path are compared, and a path in which an average of degrees of deviation is larger is given a higher priority. Alternatively, a maximum one of degrees of deviation of peculiar values of respective nodes in one path and a maximum one of degrees of deviation of peculiar values of respective nodes in another path are compared, and a path in which a maximum one of degrees of deviation is larger is given a higher priority.

Figure 10:
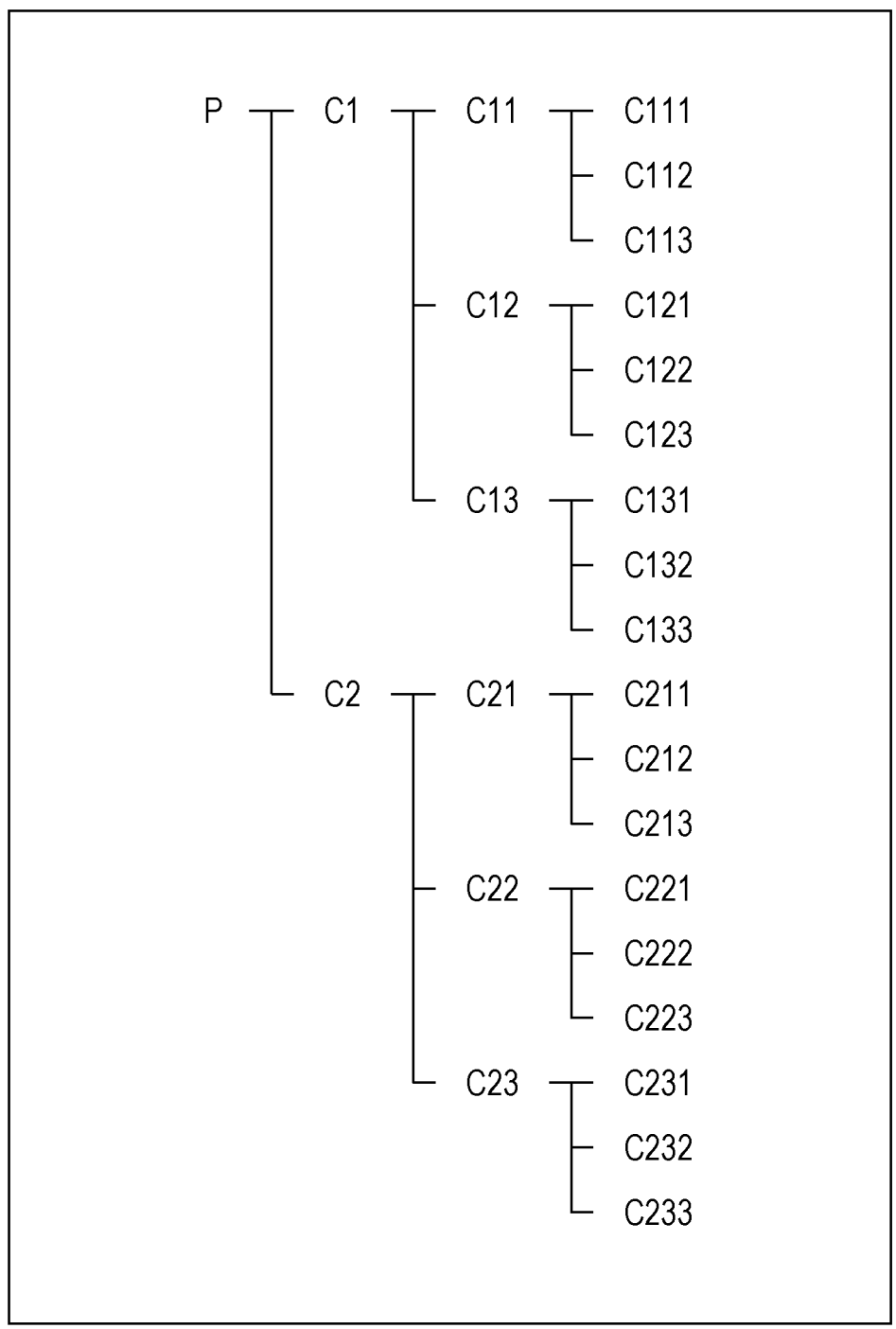
FIG. 10 schematically illustrates a configuration of a product.

FIG. 10 schematically illustrates a configuration of a product. In FIG. 10, the configuration of the product is illustrated by using a tree diagram. In the tree diagram of FIG. 10, a root node "P" represents the product. A node "C" represents a component. An affix added to a node "C" represents a hierarchical structure in an assembling relationship between components. For example, a node "C1" and a node "C2" are components in the same level that are directly joined to the product. A node "C11", a node "C12", and a node "C13" are components in the same level that are joined to the node "C1".

Figure 11:
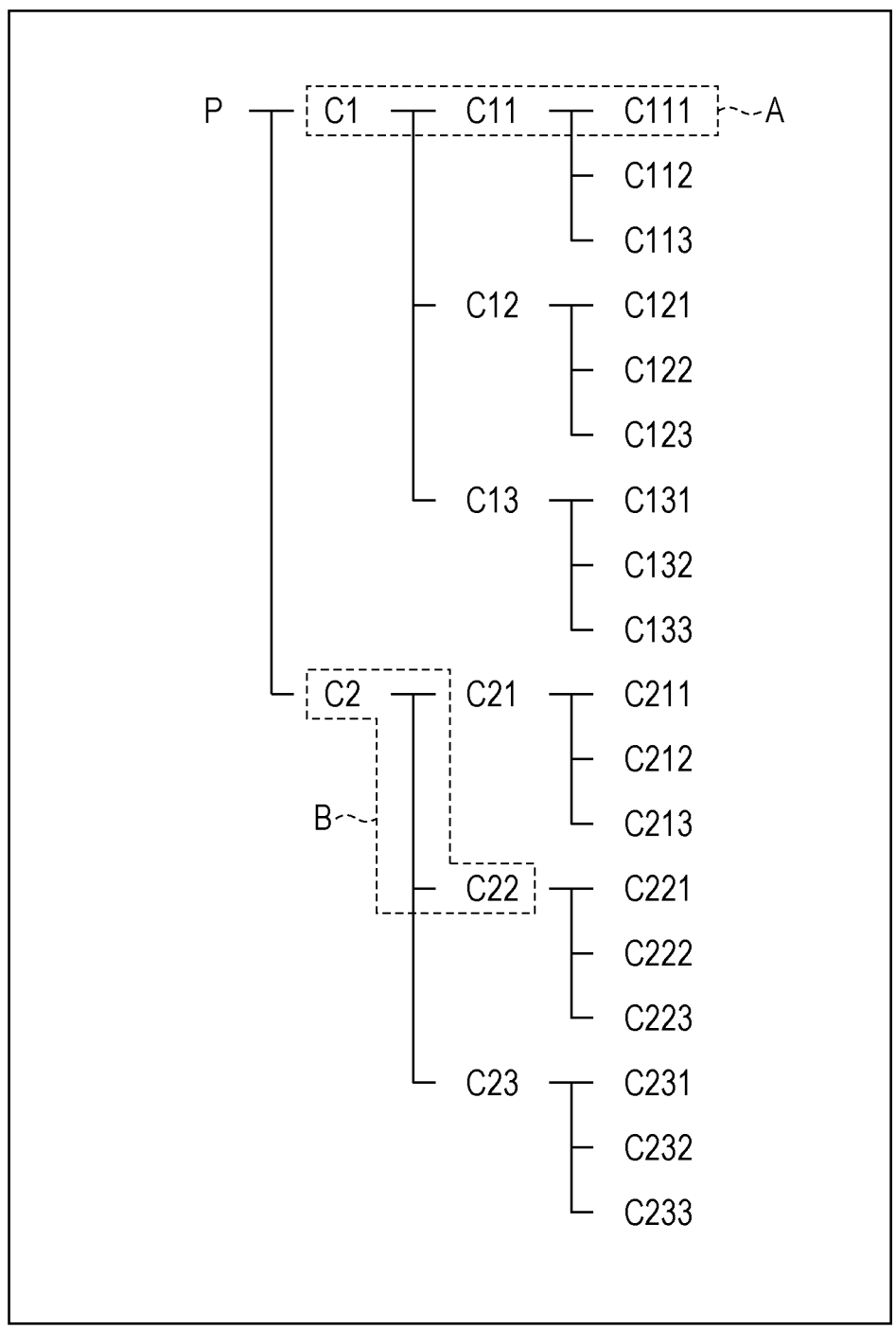
FIG. 11 illustrates an example in which plural paths are evaluated as being defect cause candidates in the configuration of the product illustrated in FIG. 10.

FIG. 11 illustrates an example in which plural paths are evaluated as being defect cause candidates in the configuration of the product illustrated in FIG. 10. In the example illustrated in FIG. 11, a path A including three nodes: node "C1"-node "C11"-node "C111" and a path B including two nodes: node "C2"-node "C22" are defect cause candidates. When the path A and the path B are compared, the path A is longer (includes a larger number of successive nodes that are peculiar value elements). Accordingly, a priority of the path A is evaluated as being higher than a priority of the path B.

Figure 12:
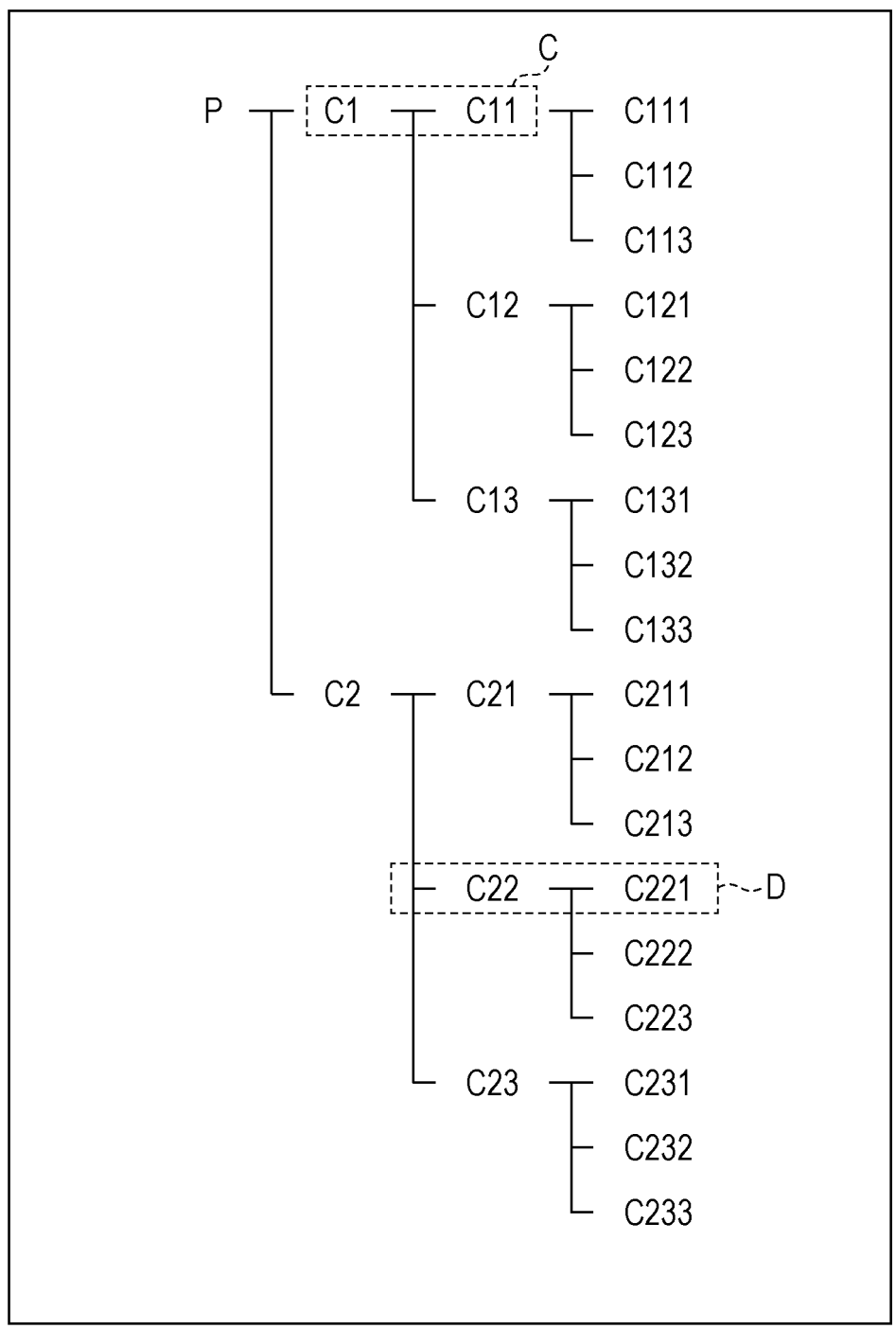
FIG. 12 illustrates another example in which plural paths are evaluated as being defect cause candidates in the configuration of the product illustrated in FIG. 10.

FIG. 12 illustrates another example in which plural paths are evaluated as being defect cause candidates in the configuration of the product illustrated in FIG. 10. In the example illustrated in FIG. 12, a path C including two nodes: node "C1"-node "C11" and a path D including two nodes: node "C22"-node "C221" are defect cause candidates. When the path C and the path D are compared, the path C and the path D have the same length. However, the path C is located at a position (level) closer to the root node "P". Accordingly, a priority of the path C is evaluated as being higher than a priority of the path D.

Figure 13:
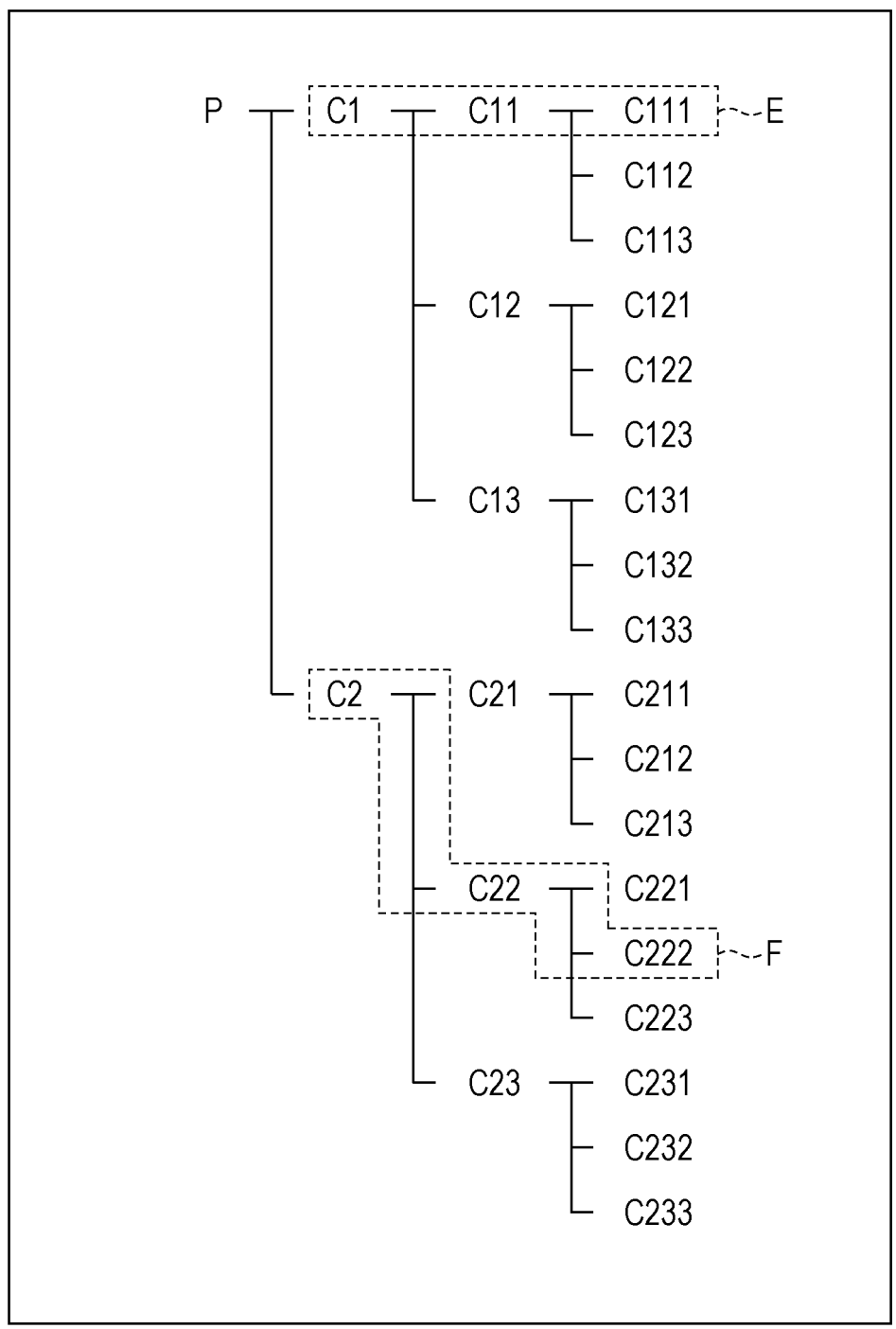
FIG. 13 illustrates another example in which plural paths are evaluated as being defect cause candidates in the configuration of the product illustrated in FIG. 10.

FIG. 13 illustrates another example in which plural paths are evaluated as being defect cause candidates in the configuration of the product illustrated in FIG. 10. In the example illustrated in FIG. 13, a path E including three nodes: node "C1"-node "C11"-node "C111" and a path F including three nodes: node "C2"-node "C22"-node "C222" are defect cause candidates. When the path E and the path F are compared, the path E and the path F have the same length. Furthermore, the path E and the path F are located at the same position (same position (same level) relative to the root node "P"). It is assumed here that when an average of degrees of deviation of peculiar values of the nodes included in each path is calculated, the average is 90% in the path E and 70% in the path F. That is, the path E is larger in average of degrees of deviation of peculiar values of the nodes. Accordingly, a priority of the path E is evaluated as being higher than a priority of the path F.

Output of Evaluation Result

Next, output of a result of evaluation of a path is described. The evaluation result output unit 160 presents, to a user of the quality control apparatus 100, a defect cause candidate as a result of the aforementioned evaluation conducted on a product in which a quality defect has been detected. For example, the evaluation result output unit 160 displays a configuration diagram illustrating a configuration of the product and explicitly shows, on this configuration diagram, a part corresponding to a path evaluated as being a defect cause candidate. For example, the evaluation result output unit 160 may output information on a defect cause candidate as an evaluation result by displaying the configuration of the product by using a tree diagram like the one illustrated in FIG. 10 so that a path evaluated as being a defect cause candidate is displayed in a form different from the other parts. For example, as illustrated in FIGS. 11 through 13, an edge and nodes that constitute a path evaluated as being a defect cause candidate may be displayed in a thicker type than the other parts. Alternatively, a path evaluated as being a defect cause candidate may be displayed in a color different from other paths or a range of a path evaluated as being a defect cause candidate may be shaded.

In a case where plural defect cause candidate paths are detected, the evaluation result output unit 160 presents defect cause priorities of the respective paths when outputting an evaluation result. For example, the evaluation result output unit 160 presents defect cause priorities by displaying the defect cause candidate paths in different display forms in accordance with the defect cause priorities. Specifically, the defect cause candidate paths may be displayed in different colors in accordance with the defect cause priorities. Alternatively, numbers indicative of the defect cause priorities of the respective defect cause candidate paths may be displayed in association with the defect cause candidate paths. Alternatively, only a predetermined number of paths may be selectively presented on the tree diagram in order of descending priority on the basis of the defect cause priorities of the respective paths.

When outputting an evaluation result, the evaluation result output unit 160 may display information on a degree of deviation in association with a defect cause candidate path. Furthermore, test values of components included in a defect cause candidate path and attribute information of an apparatus and a worker concerning work performed on the components may be displayed in association with the defect cause candidate path. Furthermore, degrees of deviation, test values, attribute information, and the like may also be displayed for a path other than a defect cause candidate. These pieces of information may be displayed when a specific path is designated by a user of the quality control apparatus 100 instead of displaying these pieces of information from the start. For example, the user designates a desired path by operating the input device 205 of the computer 200 illustrated in FIG. 6. The evaluation result output unit 160 receives designation of a path and displays information such as test values, attribute information, and degrees of deviation concerning components included in the designated path in association with the designated path. In a case where a configuration of a product is displayed by using a tree diagram like the one illustrated in FIG. 10, the evaluation result output unit 160 may display, upon designation of one or more nodes that constitute the tree diagram, information such as test values, attribute information, and degrees of deviation concerning components corresponding to the designated nodes in association with the designated nodes.

In a case where a peculiar value element is given a score in accordance with a degree of deviation of a test value of a component or attribute information of an apparatus and a worker concerning work performed on the component from a standard value in the determining process concerning a peculiar value, this score may be displayed in association with a node corresponding to the peculiar value element. Paths including nodes that are peculiar value elements may be displayed in different forms in accordance with scores. In this case, only a predetermined number of paths may be displayed in order of descending score based on a degree of deviation, or only a path including nodes that are peculiar value elements whose score based on a degree of deviation is equal to or larger than a predetermined threshold value may be displayed.

Output of an evaluation result is not limited to the above output methods, provided that a result of evaluation of a cause of a defect of a product can be presented. For example, an evaluation result may be presented by displaying only a defect cause candidate path instead of displaying the defect cause candidate path on a configuration diagram such as a tree diagram illustrating a whole configuration of a product. Alternatively, an evaluation result may be presented by displaying a list of information on components and work performed on the components that are elements constituting a defect cause candidate path.

Although the embodiment of the present invention has been described above, the technical scope of the present invention is not limited to the exemplary embodiment. Various changes and replacement of constituent members are encompassed within the present invention without departing from the scope of the technical idea of the present invention. For example, in the above exemplary embodiment, the quality control apparatus 100 includes the assembling management information DB 110, the test value DB 120, and the step-related information DB 130 and hold assembling management information, test values, and step-related information. Alternatively, the information acquisition controller 150 may acquire these pieces of information from an external server in which these pieces of information are held when a product in which a quality defect has been detected is analyzed.

The foregoing description of the exemplary embodiment of the present invention has been provided for the purposes of illustration and description. It is not intended to be exhaustive or to limit the invention to the precise forms disclosed. Obviously, many modifications and variations will be apparent to practitioners skilled in the art. The embodiment was chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. A quality control apparatus comprising:
at least one processor programmed to function as:
   a test value acquisition unit that acquires test values of respective components that constitute a product;
   an assembling management information acquisition unit that acquires assembling management information that is information concerning assembling of the product and the components; and
   a step-related information acquisition unit that acquires step-related information that is information related to a production step, the step-related information including information of a learning level of a worker assembling at least a part of the product during the production step, the learning level of the worker assessed using a skill test; and
a display that displays a configuration diagram of the product that is hierarchically constituted by the components and shows a combination of elements that are assumed to be likely to have caused a quality defect of the product on the configuration diagram on a basis of the test values, the assembling management information, and the step-related information.

2. The quality control apparatus according to claim 1, wherein
in a case where there are a plurality of combinations of elements that are assumed to be likely to have caused the quality defect of the product, the display displays information on defect cause priorities determined in accordance with a predetermined rule in association with the respective combinations.

3. The quality control apparatus according to claim 2, wherein
the display displays the plurality of combinations of elements in different display forms in accordance with the defect cause priorities.

4. The quality control apparatus according to claim 1, wherein
the display displays, as the configuration diagram, a tree diagram representing a relationship among the components that constitute the product by using nodes that correspond to the product and the components of the product and edges that represent relationships between the product and a component and between components.

5. The quality control apparatus according to claim 4, wherein
in a case where a node that constitute the tree diagram is designated, the display displays information concerning a component corresponding to the designated node in association with the designated node.

6. A quality control apparatus comprising:
at least one processor programmed to function as:
   a test value acquisition unit that acquires test values of a product and components that constitute the product;
   a step-related information acquisition unit that acquires step-related information that is information related to a production step, the step-related information including information of a learning level of a worker assembling at least a part of the product during the production step, the learning level of the worker assessed using a skill test; and
   a specifying unit that specifies a combination of elements that meet a predetermined condition on a basis of degrees of deviation of the test values and the step-related information from standard values.

7. The quality control apparatus according to claim 6, wherein the at least one processor is additionally programmed to function as an assembling management information acquisition unit that acquires assembling management information that is information concerning assembling of the product and the components,
wherein the specifying unit specifies the combination of elements including a plurality of components on a basis of a relationship between the components that constitute the product that is specified by the assembling management information.

8. The quality control apparatus according to claim 7, wherein
the combination of elements including the plurality of components includes a plurality of components belonging to different levels among the components that hierarchically constitute the product.

9. The quality control apparatus according to claim 6, wherein the at least one processor is additionally programmed to function as an output unit that outputs information indicative of the elements specified by the specifying unit as elements that are assumed to be likely to have caused a quality defect of the product.

10. The quality control apparatus according to claim 9, wherein the at least one processor is additionally programmed to function as an assembling management information acquisition unit that acquires assembling management information that is information concerning assembling of the product and the components,
wherein the output unit displays a tree diagram illustrating a hierarchical structure of the product hierarchically constituted by the components on a basis of the assembling management information and shows the elements specified by the specifying unit on the tree diagram.

11. The quality control apparatus according to claim 10, wherein
- the specifying unit gives information on degrees of deviation of the elements to the specified combination of elements; and
- the output unit displays the information on the degrees of deviation given by the specifying unit in association with a part specified by the specifying unit on the tree diagram.

12. The quality control apparatus according to claim 6, wherein
- in a case where there are a plurality of combinations of elements that meet the predetermined condition, the specifying unit determines priorities of the plurality of combinations in accordance with a predetermined rule.

13. The quality control apparatus according to claim 1, wherein the product is a multi-function printer, and the step-related information is information related to joining of components of the multi-function printer during assembly.

14. The quality control apparatus according to claim 6, wherein the product is a multi-function printer, and the step-related information is information related to joining of components of the multi-function printer during assembly.

* * * * *